US012576173B2

(12) United States Patent
Gonabal

(10) Patent No.: US 12,576,173 B2
(45) Date of Patent: Mar. 17, 2026

(54) FLEXIBLE UVC DISINFECTANT DEVICE

(71) Applicant: HONEYWELL INTERNATIONAL INC., Charlotte, NC (US)

(72) Inventor: Srinivas D. Gonabal, Charlotte, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 1125 days.

(21) Appl. No.: 17/644,992

(22) Filed: Dec. 17, 2021

(65) Prior Publication Data

US 2022/0193286 A1 Jun. 23, 2022

(30) Foreign Application Priority Data

Dec. 21, 2020 (IN) .............................. 202011055565

(51) Int. Cl.
*A61L 2/10* (2006.01)

(52) U.S. Cl.
CPC ............. *A61L 2/10* (2013.01); *A61L 2202/11* (2013.01); *A61L 2202/14* (2013.01)

(58) Field of Classification Search
CPC ....................................................... A61L 2/10
See application file for complete search history.

(56) References Cited

U.S. PATENT DOCUMENTS 7,989,779 B1 8/2011 Ray et al.
8,895,940 B2 11/2014 Moskowitz et al.

9,649,398 B1 5/2017 York
D823,430 S 7/2018 York
10,092,669 B2 10/2018 Marshall
10,183,084 B2 1/2019 Cahan et al.
10,751,435 B2 8/2020 Wyman et al.
D895,764 S 9/2020 York
10,987,440 B1 * 4/2021 Sood ..................... F04D 29/646
2011/0174992 A1 7/2011 Sakita
(Continued)

FOREIGN PATENT DOCUMENTS

KR 102167793 B1 * 10/2020 .............. A61L 2/24
WO 2013025894 A2 2/2013
WO 2016004205 A2 1/2016

OTHER PUBLICATIONS

English translation of KR-102167793 B1 (Year: 2020).*
(Continued)

*Primary Examiner* — Sean E Conley
(74) *Attorney, Agent, or Firm* — Seager, Tufte & Wickhem, LLP

(57) ABSTRACT

A device configured for disinfecting a desired touchpoint may include a flexible housing, which may be field configurable into two or more different shapes to accommodate the desired touchpoint. The flexible housing may house a plurality of ultraviolet-C (UVC) light-emitting diodes (LEDs), a power source, and a controller which may be operatively coupled to the plurality of UVC LEDs, the power source, and a motion sensor. In response to receiving a motion signal from the motion sensor indicating motion near the desired touchpoint, the controller waits until the motion sensor no longer detects motion and then activates one or more of the plurality of UVC LEDs for a predetermined period of time to disinfect the desired touchpoint.

20 Claims, 10 Drawing Sheets

(56)             References Cited

U.S. PATENT DOCUMENTS

| 2016/0249436 | A1  | 8/2016 | Inskeep |
| 2022/0125976 | A1* | 4/2022 | Hughes ................ E05B 1/0069 |

OTHER PUBLICATIONS

"The Handle Attendant™ kills 99.9% of viruses, germs and bacteria in seconds with UV, UV Sterile Solutions," 5 pages, 2016.
Kalter, "Coronovirus Puts UV in the Disinfectant Spotlight," WebMD, 4 pages, 2020, Accessed on Jan. 5, 2022.
"Self Sanitizing Door Handle," James Dyson Award, 5 pages, 2019, Accessed on Sep. 29, 2020.
"Self-Sterilizing Door Handle by Bomi Choi," Home Reviews, 23 pages, Accessed Sep. 29, 2020.
"Teens Develop $13 Door Handle that Kills 99% of Germs, Gadgets," Science & Technology, 3 pages, Accessed on Sep. 29, 2020.
"Ultraviolet Germicidal Irradiation," Wikipedia, 13 pages, Accessed on Jan. 5, 2022.
"UV Door Handle," Uvway, 3 pages, Accessed Sep. 29, 2022.
"Washing Hands Not Enough: Luxars Inc. Launches UVWAY; Canada's First Self-disinfecting Door Handle," 6 pages, Accessed on Sep. 29, 2020.
Buddhi, et al., Indian Patent Application No. 202011044064, "UV Sterilization Device for Door Handles", Oct. 23, 2020 (specification 15 pgs., drawings 5 pgs).
First Office Action, India Patent Office, India Patent Application No. 202011055565, Jul. 7, 2022 (6 pgs).

\* cited by examiner

FLEXIBLE UVC DISINFECTANT DEVICE

CROSS-REFERENCE TO RELATED APPLICATIONS

This application claims priority pursuant to 35 U.S.C. 119(a) to India Patent Application No. 202011055565, filed Dec. 21, 2020, which application is incorporated herein by reference in its entirety.

TECHNICAL FIELD

The present disclosure relates generally to disinfectant devices. More particularly, the present disclosure relates to Ultra-Violet (UV) light disinfectant devices.

BACKGROUND

Public buildings such as malls, office buildings, grocery stores, etc., typically have a number of common public touch points such as door handles, door knobs, elevator buttons, and the like. Most often such common public touch points are touched by a user's bare hands. In some cases, the user may have an illness such as a common cold, influenza, COVID-19 and/or some other illness. In some cases, the user may be asymptomatic but still contagious. When such a user touches a common public touch point, such as a door handle, the user may unintentionally contaminate the touched surface. This contamination may expose subsequent users who touch the same common public touch point to the illness, thereby placing the subsequent users at risk of contracting the illness.

The recommendation from health officials is to avoid contact with common public utilities. However, this is not a feasible solution in today's world. Personal safety measures may be taken, such as, using gloves when touching common public touch points (e.g., a door handle). However, this is inconvenient. Also, if the gloves are not properly worn, removed and discarded, the user can expose him or herself to the contagions that is present on the gloves. What would be desirable is an efficient way to automatically sanitize common touch points between user visits.

SUMMARY

The present disclosure relates generally to disinfectant devices. More particularly, the present disclosure relates to Ultra-Violet (UV) light disinfectant devices.

In one example, the device may include a flexible housing, wherein the flexible housing is field configurable into two or more different shapes to accommodate a variety of different touchpoints. The flexible housing may house a plurality of ultraviolet-C (UVC) light-emitting diodes (LEDs), a power source, and a controller that is operatively coupled to the plurality of UVC LEDs, the power source and a motion sensor. In some cases, in response to receiving a first motion signal from the motion sensor, indicating motion near the desired touchpoint, the controller may be configured to wait until the motion sensor no longer detects motion, and then activates one or more of the plurality of UVC LEDs for a predetermined period of time to disinfect the desired touchpoint.

In another example, a device for disinfecting a desired touchpoint may include a flexible housing, wherein the flexible housing is field configurable to a desired geometry in order to accommodate a desired touchpoint. The flexible housing may house a plurality of individual cells, wherein each of the plurality of individual cells may include a cell ultraviolet-C (UVC) light-emitting diode (LED), a cell power source, a cell receiver, and a cell controller operatively coupled to the cell UVC LEDs, the cell power source and the cell receiver. In some cases, in response to receiving via the cell receiver a first motion signal from a remote motion sensor, indicating motion near the desired touchpoint, the cell controller may be configured to wait until the motion sensor no longer detects motion and then may activate the cell UVC LED for a predetermined period of time. In some cases, the motion sensor may be part of the cell. In other cases, the motion sensor may be remote from the cell and even remote from the device (e.g. across the room).

In another example, a method for disinfecting a desired touch point may include receiving a first motion signal indicating motion near the desired touch point. In response to receiving the first motion signal, the system may wait until motion is no longer detected near the desired touch-point, and then one or more UVC LEDs may be activated for a predetermined length of time to disinfect the desired touchpoint. In some cases, in response to receiving a second motion signal indicating motion near the desired touchpoint while one or more UVC LEDs are activated, any activated ones of the one or more UVC LEDs may be turned off.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which.

Figure 1:
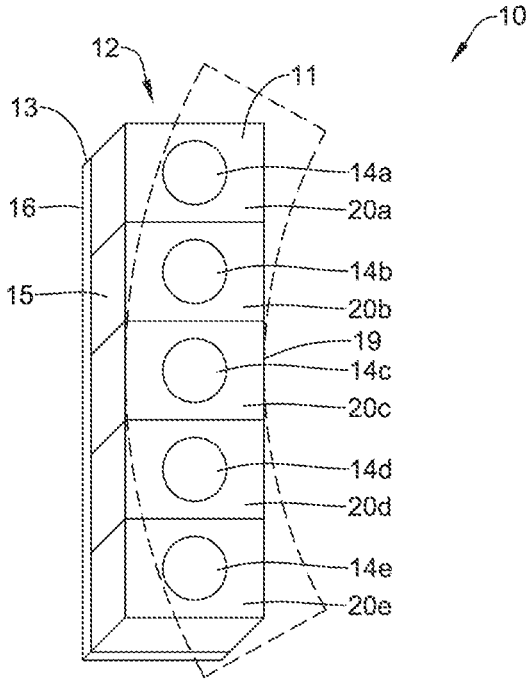
FIG. 1 is a perspective view of an illustrative Ultra-Violet (UV) light disinfectant device.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranged by endpoints includes all numbers subsumed within that range (e.g., 1 to 5 includes, 1, 1.5, 2, 2.75, 3, 3.8, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

FIG. 1 is a perspective view of an illustrative Ultra-Violet (UV) light disinfectant device for disinfecting a desired touchpoint. The touchpoint may be a common public touch point, such as a touch point that multiple people handle, contact, touch, or otherwise encounter multiple times a day. The touchpoint may include, for example but not limited to, a door knob, a door handle, an elevator button, an accessible button, a light switch, a card reader, a biometric reader, a security key pad, or any other touchpoint as desired. As shown in FIG. 1, the device 10 includes a flexible housing 12. The flexible housing 12 may be formed from a material that allows the device 10 to flex, bend, or otherwise be configurable in the field. The flexible housing 12 may include a flexible body made from a flexible silicone, plastic, polymer, rubber, or the like. It is contemplated that the flexible housing 12 may be configurable into any of a plurality of desired shapes in the field, such as but not limited to, a square, a triangle, a circle, a rectangle, an oval, etc.

In the example shown, the housing 12 includes a front 11, a back 13, and opposing sidewalls 15, 19. The housing 12 may include a thickness between the back 13 and the front 11 of 5 centimeters or less, 3 centimeters or less, 2 centimeters or less, but these are just examples. The housing 12 may be configured to house a plurality of Ultra Violet-C (UVC) light-emitting diodes (LEDs) 14a, 14b, 14c, 14d, and 14e (hereinafter generally referenced as UVC LEDs 14). While UVC LED's are used in this example, it is contemplated that any suitable UV light source suitable for disinfecting a surface may be used. While it is shown that the housing 12 may include five (5) UVC LEDs 14, it is contemplated that the housing 12 may include any suitable number of UVC LEDs 14, such as, for example, one UVC LED, twenty UVC LEDs, one hundred UVC LEDs, or any number so desired, and it may depend on the length of the housing 12. The UVC LEDs 14 may be positioned such that the desired touchpoint is exposed to the ultraviolet-C light emitted by the UVC LEDs 14 to disinfect the desired touchpoint.

As shown in FIG. 1, the UVC LEDs 14 may be positioned on the front 11 of the housing 12. When the UVC LEDs 14 are positioned on the front 11 of the housing 12, the UVC LEDs 14 may be positioned to emit light at an angle relative to the front 11 of the housing. In some cases, the UVC LEDs 14 may direct light along an axis that is perpendicular to the front 11 of the housing 12. In some cases, the UVC LEDs 14 may direct light at an angle relative to an axis that is perpendicular to the front 11 of the housing 12, such as a 30-degree angle, a 45-degree angle or a 60-degree angle. These are just examples. In some cases, some of the UVC LEDs 14 may be orientated at a different angle than other of the UVC LEDs 14. In some cases, each of the UVC LEDs 14 may have a lens that directs the light emission from the corresponding UVC LED 14. It is contemplated that the lens may produce a UV emission having a beam angle. The beam angle may be small to produce a tightly controlled beam, or may be larger to produce a disperse light emission. It is contemplated that the beam angle may be less than 5 degrees, less than 10 degrees, less than 30 degrees, less than 60 degrees, less than 80 degrees, or any other suitable beam angle.

Figure 2:
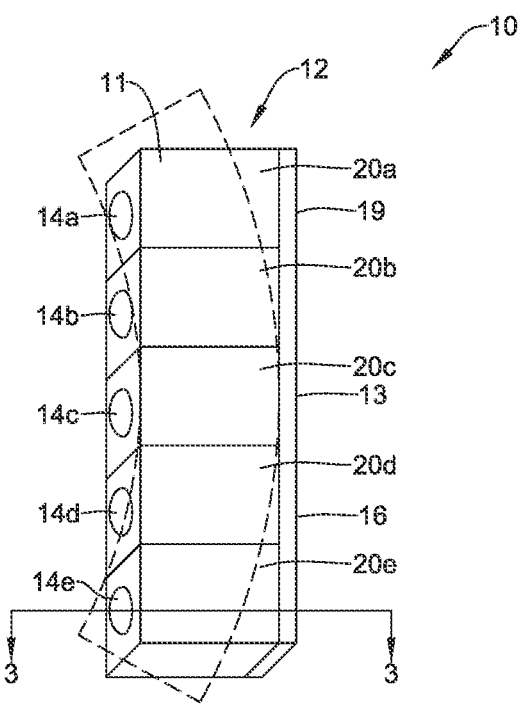
FIG. 2 is a perspective view of another illustrative Ultra-Violet (UV) light disinfectant device.

Although it is shown in FIG. 1 that the UVC LEDs 14 are positioned on the front 11 of the housing 12, it is contemplated that the UVC LEDs 14 may be positioned at any suitable location, such as, for example, along the sidewall 15 (as shown in FIG. 2). In other examples, it contemplated that the UVC LEDs may be positioned along the edge between the sidewall 15 and the front 11 and/or along the edge between the sidewall 15 and the back 13. In some cases, some of the UVC LEDs 14 may be positioned on the front 11, some along the sidewall 15, some along the edge between the sidewall 15 and the front and/or some along the sidewall 15 and the back 13. These are just examples.

In some cases, the housing 12 may include a plurality of cells 20a, 20b, 20c, 20d, and 20e (hereinafter generally referenced as cells 20). While it is shown that the housing 12 may include five (5) cells 20, it is contemplated that the housing 12 may include any suitable number of cells 20, such as, for example, one cell, twenty cells, one hundred cells, or any number so desired. It is contemplated that the flexible housing 12 may be cut to length, such as cut between adjacent cells 20, to accommodate a particular installation. Also, as shown in dotted lines in FIG. 1, the flexible housing 12 may be flexed into a curved shape in the field, with the cells 20 carried by the flexible housing 12 to lie along that curved shape. The cells 20 may have a center-to-center spacing along the length of the flexible housing 12. When so provided, the number of cells 20 at a particular installation may depend on the length of the flexible housing used at the particular installation and the center-to-center spacing of the cells.

It is contemplated that each of the cells 20 may include one or more of the UVC LEDs 14, as shown in FIG. 1. The device 10 may further include an adhesive 16 on the back 13. The adhesive 16 may be a peel off adhesive strip that is secured to the back 13 of the flexible housing 12, where a peel off strip is removed by the installer revealing the adhesive, allowing the device 10 to be easily secured to a mounting surface in any desired shape adjacent the desired touchpoint. However, this is just one example adhesive. In some cases, an adhesive is not provided, but rather the device 10 is secured to the mounting surface using screws or other securement.

FIG. 2 is a perspective view of another illustrative Ultra-Violet (UV) light disinfectant device. This embodiment is similar to the embodiment shown in FIG. 1, except the UVC LEDs 14 are positioned along the sidewall 15 of the housing 12.

Figure 3:
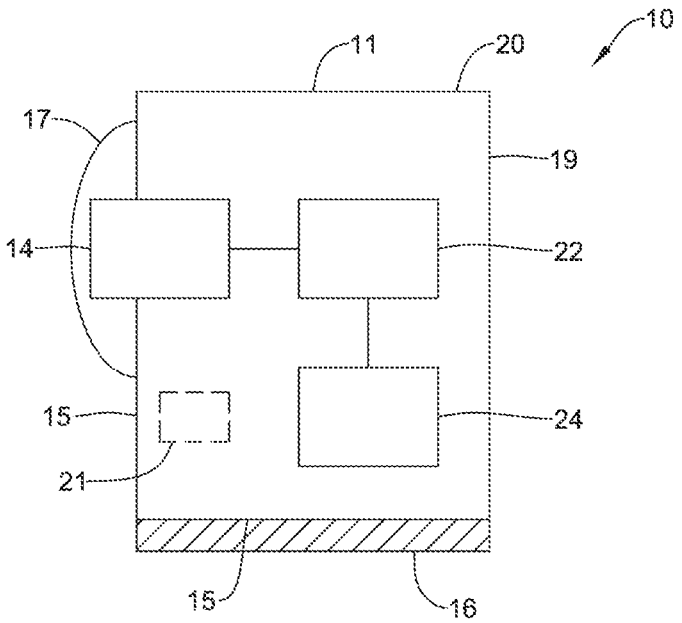
FIG. 3 is a cross-sectional view of a cell of the illustrative Ultra-Violet (UV) light disinfectant device of FIG. 2, taken along line 3-3.

FIG. 3 is a cross-sectional view of a cell of the illustrative Ultra-Violet (UV) light disinfectant device of FIG. 2, taken along line 3-3. As discussed above, the plurality of cells 20 are housed by the flexible housing 12, and the flexible housing 12 may include any suitable number of cells 20. As shown in FIG. 3, each of the cells 20 may include one or more of the UVC LEDs 14, a lens 17, a power source 22, and electronics 24. In some cases, the cells 20 may include a motion sensor 27, but this is not required. The power source 22 may include a battery, a supercapacitor, line power, or any other suitable power source. The electronics 24 may include a processor, a memory, a receiver, a wired trans-ceiver, a wireless transceiver (e.g. Bluetooth, WIFI, etc.) and/or any other suitable component. In the example shown, the electronics 24 is operatively coupled to the power source 22 and to the UVC LEDs 14. It is contemplated that the electronics 24 may communicate with the one or more components (e.g., the power source 22, the UVC LEDs, or the motion sensor 27) via one or more wired or wireless links (not shown). Additionally, the electronics 24 may communicate over one or more wired or wireless networks that may accommodate remote access and/or control of the electronics 24 via another device such as a smart phone, tablet, e-reader, laptop computer, personal computer, or the like. In some cases, the network may be a wireless local area network (LAN). In some cases, the network may be a wide area network (WAN) including, for example, the Internet. In some cases, the wireless local area network may provide a wireless access point and/or a network host device that is separate from the electronics 24. In other cases, the wireless local area network may provide a wireless access point and/or a network host device that is part of the electronics 24. In some cases, the wireless local area network may include a local domain name server (DNS), but this is not required for all embodiments. In some cases, the wireless local area network may be an ad-hoc wireless network, but this is not required.

Figure 4:
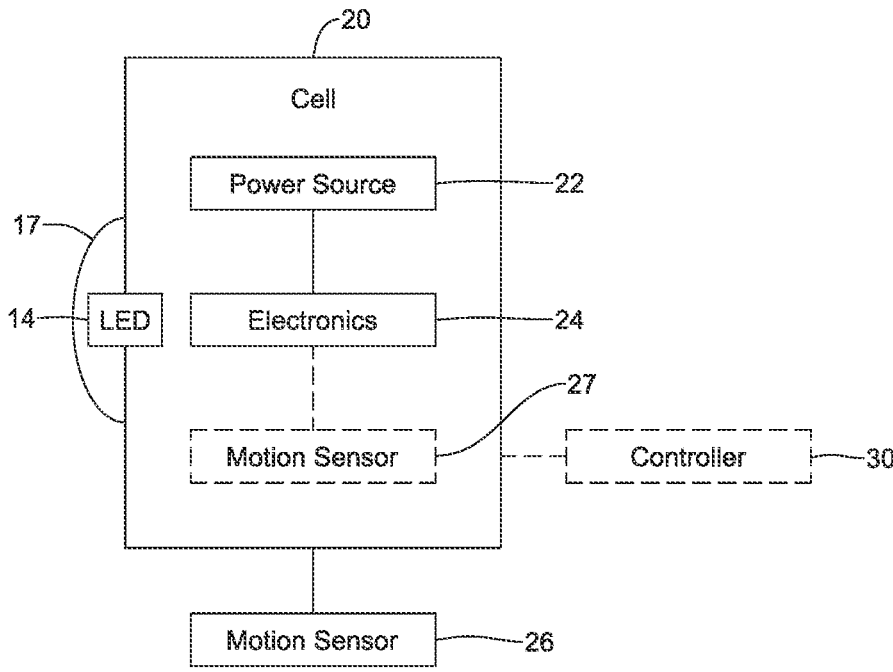
FIG. 4 is a schematic block diagram of an illustrative cell of the illustrative Ultra-Violet (UV) light disinfectant device of FIG. 2.

FIG. 4 is a schematic block diagram of an illustrative cell of the illustrative Ultra-Violet (UV) light disinfectant device of FIG. 2. As discussed with reference to FIG. 3, each cell 20 may be one of the plurality of cells 20 that are housed by the flexible housing 12. As shown in FIG. 4, each of the cells 20 may include one or more of the UVC LEDs 14, the lens 17, the power source 22, and the electronics 24. In some cases, the electronics 24 may include a controller, a receiver, a transceiver, a circuit board, or the like. In some cases, the controller 30 may be remote from the cells 20. In some cases, the motion sensor 27 may be disposed within the cells 20, thus housed by the flexible housing 12, but this is not required. In some cases, the motion sensor may be located separately from the cells 20 of the flexible housing 12, as indicated by the motion sensor 26. The motion sensor 26 may be located along a periphery of the area that monitors the desired touchpoint. The motion sensor 26 may be operatively coupled to the controller 30 and/or the electronics 24 via a wired or wireless communication link. In some cases, the controller 30 may be separate from the cells 20. In some cases, a single controller may control more than one cell 20. In some cases, the controller 30 may be included in the electronics 24 within each of the cells 20.

In use, the flexible housing 12 of the device 10 is configured to be field configurable to a desired geometry to accommodate a desired touchpoint (e.g., a door handle) encountered in the field. The flexible housing 12 may be cut to length, such as between two adjacent cells 20, to achieve the desired length for the device 10. The housing 12 is then secured to a surface adjacent the desired touchpoint. The housing 12 may be secured to the surface via the adhesive 16 and/or any other securement. The adhesive 16 may be any suitable adhesive (e.g., glue, double-sided tape, etc.).

The UVC LEDs 14 may be positioned within the flexible housing 12 such that they are angled toward the desired touchpoint. In some cases, the motion sensor 27 and/or the motion sensor 26 may detect motion at or near the touch-point (e.g., indicating a user has or will likely contact a door handle) and may send a first motion signal to the controller 30. In some cases, the motion sensor 27 and/or the motion sensor 26 may be configured to send the first motion signal to the controller 30. The controller 30 may then wait until the motion sensor 27 no longer detects motion. When the motion sensor 27 and/or the motion sensor 26 no longer detects motion (e.g., the user has left the area), the controller 30 may send an instruction to the electronics 24 (e.g., via the cell receiver) to activate one or more of the plurality of UVC LEDs 14 for a predetermined period of time to disinfect the desired touchpoint. The predetermined period of time may include any suitable time period such as but not limited to, five seconds, ten seconds, twenty seconds, thirty seconds, etc. In some cases, the period of time is field programmable and may depend on the installation.

In some cases, while the UVC LEDs 14 are activated, the motion sensor 27 and/or the motion sensor 26 may detect a subsequent motion (e.g., a subsequent user has or will likely contact the door handle) and then send a second motion signal indicating motion at or near the desired touchpoint to the controller 30. The controller 30 may then turn off any activated ones of the plurality of UVC LEDs 14 to help prevent the subsequent user from being exposed to the UV light emission. When the motion sensor 27 and/or the motion sensor 26 no longer detects motion, the controller 30 may then re-activate one or more of the plurality of UVC LEDs 14 for a predetermined period of time to disinfect the desired touchpoint. When the predetermined period of time has expired, the controller 30 may turn off any activated ones of the plurality of UVC LEDs 14.

Because UV light is not visible, it is contemplated that the device 10 may include a visible LED light that can be seen by a user that indicates that the UVC LEDs 14 of the device 10 are activated or not (not shown). This visible LED light may be turned on by the controller when the UVC LEDs 14 of the device 10 are turned on and active, and may be turned off (or turned to a different color) when the UVC LEDs 14 are turned off and not active. In some cases, the visible LED light that can be seen by the user may emit a red color when the UVC LEDs 14 are activated (e.g., the UVC LEDs 14 are disinfecting the desired touchpoint). In some cases, the visible LED light may emit a green color when the UVC LEDs 14 are turned off. In some cases, the visible LED light may emit an orange or yellow color to indicate that the power source 22 needs to be charged or replaced. These are examples.

In some cases, the cells 20 may each include the UVC LEDs 14, the electronics 24 including a controller, the power source 22, and the motion sensor 27, and may operate independently from one another. When the cells 20 operate independently from one another, the cells 20 may still communicate with one another via receivers/transceivers (e.g., the electronics 24), but this is not required. For example, if one cell detects motion, this information may be passed onto the other cells 20. In some cases, the cells 20 may each include the UVC LEDs 14, the power source 22, and the electronics 24, but may not operate independently from one another. In such cases, the cells 20 may be connected to one another via a master controller (which may be, for example, controller 30).

Figure 5:
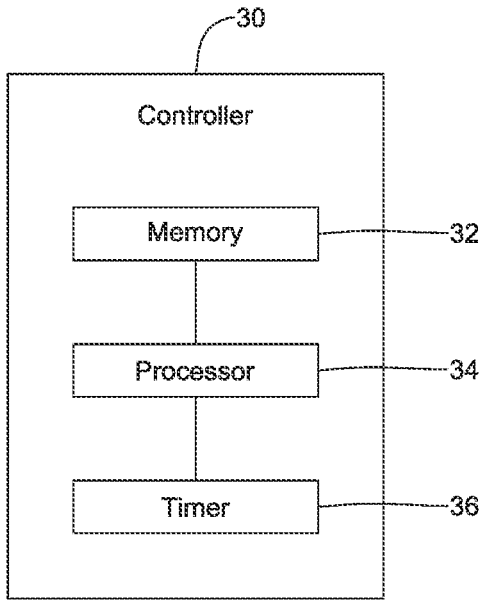
FIG. 5 is a schematic block diagram of an illustrative controller.

FIG. 5 is a schematic block diagram of the illustrative controller 30 of FIG. 4. As shown in FIG. 5, the controller 30 may include a memory 32, a processor 34, and a timer 36. The memory 32 may be a non-transitory computer-readable, and may be configured to store one or more programs within the memory 32. The memory 32 may also store software that is used to provide the functionality of the timer 36. The memory 32 may be any suitable type of storage device including, but not limited to, RAM, ROM, EPROM, flash memory, and/or the like. The processor 34 may be a micro-processor, and may be operatively coupled to the memory 32 and the timer 36. The processor 34 may be configured to receive signals from the motion sensor 26 and/or the motion sensor 27 located throughout the area.

Depending upon the application and/or where the device 10 is located, remote access and/or control of the controller 30 may be provided over a first network and/or a second network. A variety of remote wireless devices may be used to access and/or control the controller 30 from a remote location (e.g., remote from the controller 30) over the first network and/or the second network including, but not limited to, mobile phones including smart phones, tablet computers, laptop or personal computers, wireless network-enabled key fobs, e-readers, and/or the like. In many cases, the remote wireless devices are configured to communicate wirelessly over the first network and/or the second network with the controller 30 via one or more wireless communication protocols including, but not limited to, cellular communication, ZigBee, REDLINK™, Bluetooth, WiFi, IrDA, dedicated short range communication (DSRC), EnOcean, and/or any other suitable common or proprietary wireless protocol, as desired. In some cases, the network may be a wide area network or global network (WAN) including, for example, the Internet. In some cases, the wireless local area network may provide a wireless access point and/or a network host device that is separate from the controller 30. In other cases, the wireless local area network may provide a wireless access point and/or a network host device that is part of the controller 30. In some cases, the wireless local area network may include a local domain name server (DNS), but this is not required for all embodiments. In some cases, the wireless local area network may be an ad-hoc wireless network, but this is not required.

FIGS. 6-9 are schematic views of the illustrative device 10 in various example configurations around desired touch-points 18. The embodiments shown in FIGS. 6-9 are examples. It is contemplated that the device 10 may be configured to accommodate any suitable touchpoint such as, but not limited to, a door knob, a door handle, an elevator button, an accessible button, a light switch, a card reader, a biometric reader, a security key pad, or any other touchpoint as desired.

Figure 6:
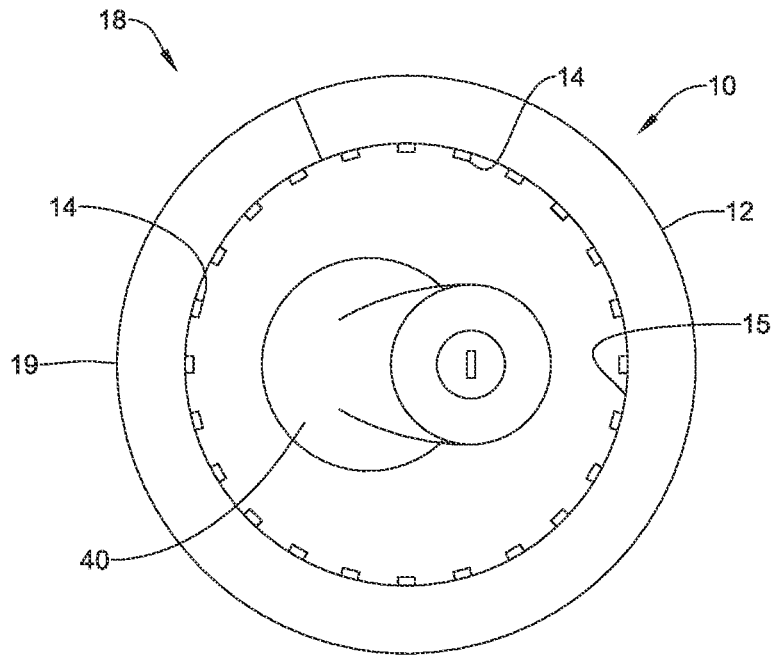
FIG. 6 is a schematic view of the illustrative Ultra-Violet (UV) light disinfectant device of FIG. 2 configured in the field around a door knob.

FIG. 6 illustrates the device 10 in which the flexible housing 12 has been configured to accommodate the geometry of a knob 40. The UVC LEDs 14 of the housing 12 are shown positioned on the sidewall 15 of the housing 12 and are angled toward the knob 40 so as to expose the knob 40 to the UVC light to disinfect the knob 40 after a user has contacted the knob 40.

Figure 7:
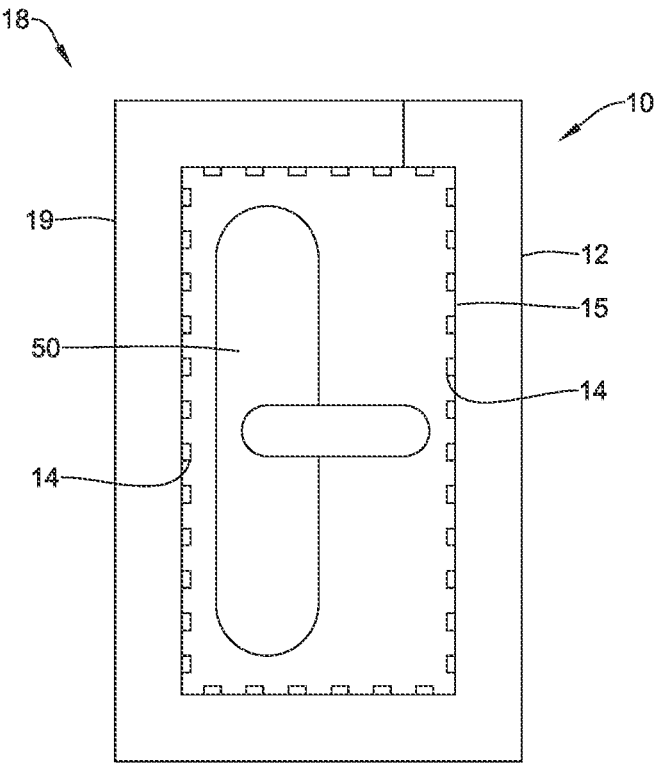
FIG. 7 is a schematic view of the illustrative Ultra-Violet (UV) light disinfectant device of FIG. 2 configured in the field around a door handle.

FIG. 7 illustrates the device 10 in which the flexible housing 12 has been configured to accommodate the geometry of a door handle 50. The UVC LEDs 14 of the housing 12 are shown positioned on the sidewall 15 of the housing 12 and are angled toward the handle 50 so as to expose the handle 50 to the UVC light to disinfect the handle 50 after a user has contacted the handle 50.

Figure 8:
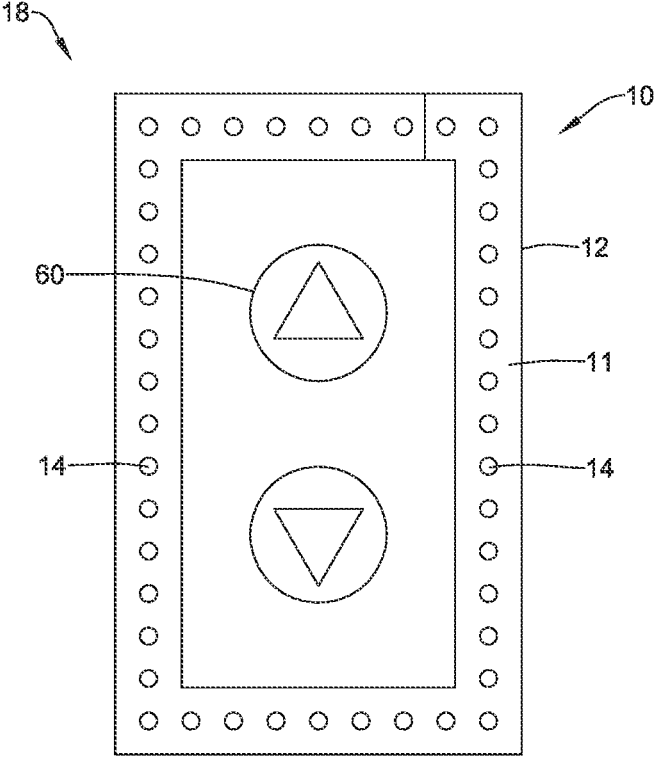
FIG. 8 is a schematic view of the illustrative Ultra-Violet (UV) light disinfectant device of FIG. 1 configured in the field around a set of elevator buttons.

FIG. 8 illustrates the device 10 in which the flexible housing 12 has been configured to accommodate the geometry of a set of elevator buttons 60. The UVC LEDs 14 of the housing 12 are positioned on the front 11 of the housing 12 and are angled toward the button 60 so as to expose the button 60 to the UVC light to disinfect the button 60 after a user has contacted the button 60.

Figure 9:
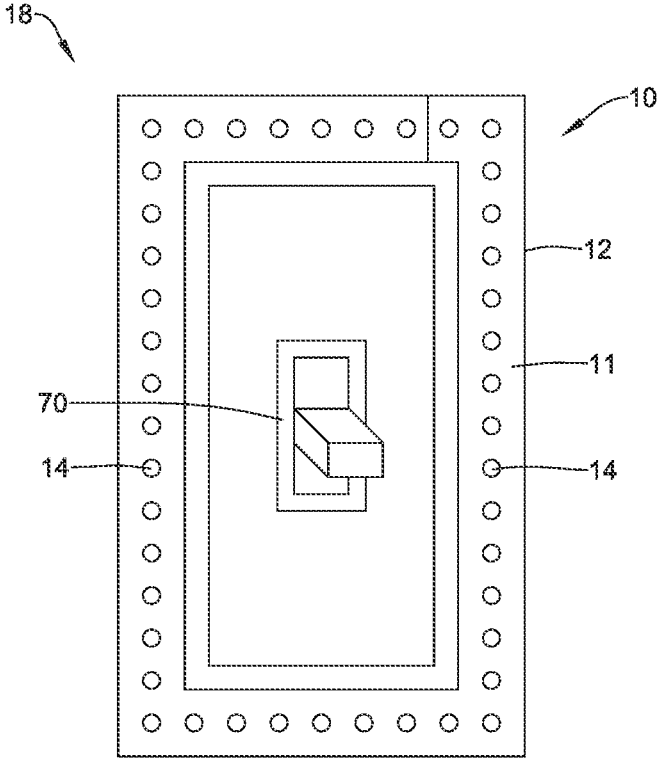
FIG. 9 is a schematic view of the illustrative Ultra-Violet (UV) light disinfectant device of FIG. 1 configured in the field around a light switch; and, FIG. 10 is a flow chart showing an illustrative method of disinfecting a desired touchpoint.

FIG. 9 illustrates the device 10 in which the flexible housing 12 has been configured to accommodate the geometry of a light switch 70. The UVC LEDs 14 of the housing 12 are positioned on the front 11 of the housing 12 and are angled toward the switch 70 so as to expose the switch 70 to the UVC light to disinfect the switch 70 after a user has contacted the switch 70.

Figure 10:
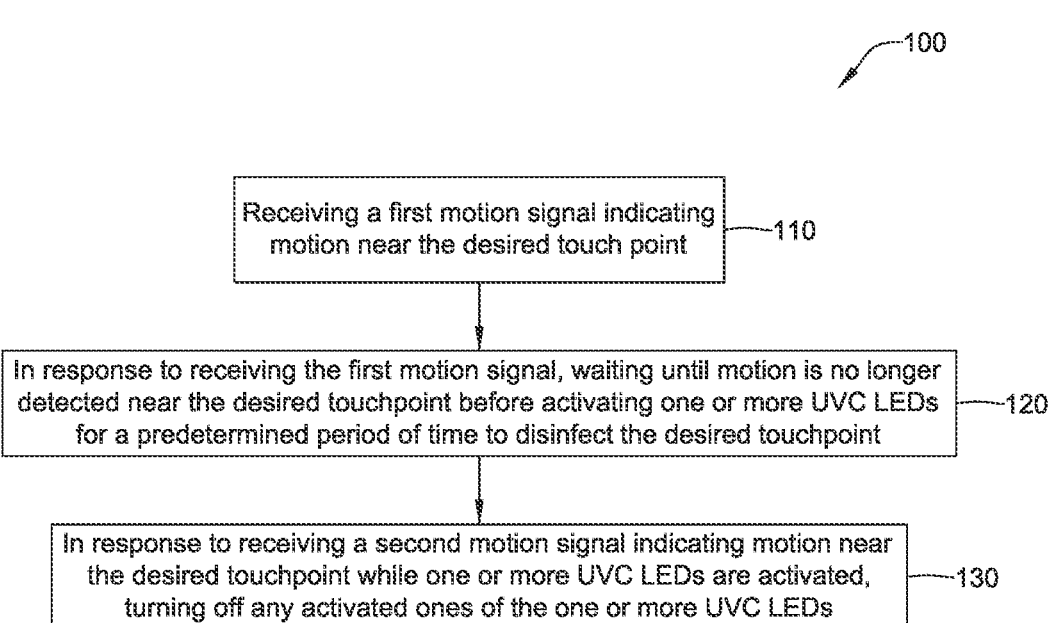

FIG. 10 is a flow chart showing an illustrative method 100 of disinfecting a desired touchpoint. The illustrative method 100 includes receiving a first motion signal indicating motion near the desired touchpoint, as referenced by block 110. In response to receiving the first motion signal, the method 100 waits until motion is no longer detected near the desired touchpoint, and then activating one or more UVC LEDs for a predetermined period of time to disinfect the desired touchpoint, as referenced by block 120. In response to receiving a second motion signal indicating motion near the desired touchpoint while one or more UVC LEDs are activated, the illustrative method 100 includes turning off any activated ones of the one or more UVC LEDs, as referenced by block 130.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A device for disinfecting a desired touchpoint, the device comprising:

a flexible housing, wherein the flexible housing is field configurable into two or more different shapes to accommodate the desired touchpoint;

a plurality of ultraviolet-C (UVC) light-emitting diodes (LEDs) housed by the flexible housing;

a power source housed by flexible housing; and a controller housed by the flexible housing and operatively coupled to the plurality of UVC LEDs, the power source, and a motion sensor, wherein the controller is configured to:

a) receive a first motion signal from the motion sensor indicating motion near the desired touchpoint;

b) in response to receiving the first motion signal, wait until the motion sensor no longer detects motion; and c) after determining the motion sensor no longer detects motion, activate one or more of the plurality of UVC LEDs for a predetermined period of time to disinfect the desired touchpoint.

2. The device of claim 1, wherein in response to receiving a second motion signal from the motion sensor indicating motion near the desired touchpoint while the plurality of UVC LEDs are activated, the controller is configured to turn off any activated ones of the plurality of UVC LEDs.

3. The device of claim 1, wherein the motion sensor is housed separately from the flexible housing and is operatively coupled to the controller.

4. The device of claim 1, wherein the motion sensor is housed by the flexible housing.

5. The device of claim 1, wherein the motion sensor is operatively coupled to the controller via a wired or wireless communication link.

6. The device of claim 1, wherein the flexible housing comprises silicone that is field configurable into two or more different shapes.

7. The device of claim 1, wherein the flexible housing comprises plastic that is field configurable into two or more different shapes.

8. The device of claim 1, wherein the flexible housing is field configurable into a desired shape, and wherein the device further comprises an adhesive for securing the flexible housing in the desired shape adjacent to the desired touchpoint.

9. The device of claim 1, wherein the flexible housing is configured to be flexed in the field into two or more different shapes.

10. The device of claim 1, wherein the plurality of UVC LEDs are positioned in the flexible housing to expose the desired touchpoint to UVC light to disinfect the desired touchpoint when the plurality of UVC LEDs are activated by the controller.

11. The device of claim 1, wherein the flexible housing includes a plurality of cells and each of the plurality of cells includes one or more of the plurality of UVC LEDs and a power source.

12. The device of claim 11, wherein each of the plurality of cells further includes a controller and a transceiver, wherein the controllers of the plurality of cells communicate with one another via the transceiver.

13. The device of claim 1, wherein the desired touchpoint is at least one of a knob, a handle, a switch, and a button.

14. A device for disinfecting a desired touchpoint, the device comprising:

a flexible housing, wherein the flexible housing is field configurable to accommodate a desired geometry to accommodate the desired touchpoint;

a plurality of individual cells housed by the flexible housing, wherein each of the plurality of individual cells comprises:

a cell ultraviolet-C (UVC) light-emitting diode (LED);

a cell power source;

a cell receiver;

a cell controller operatively coupled to the cell UVC LEDs, the cell power source, and the cell receiver, wherein in response to receiving via the cell receiver a first motion signal from a motion sensor indicating motion near the desired touchpoint, the cell controller is configured to wait until the motion sensor no longer detects motion and then activates the cell UVC LED for a predetermined period of time.

15. The device of claim 14, wherein in response to receiving via the cell receiver a second motion signal from the motion sensor indicating motion near the desired touchpoint while the cell UVC LED is activated, the cell controller is configured to turn off the cell UVC LED.

16. The device of claim 14, wherein the motion sensor is a cell motion sensor.

17. The device of claim 14, wherein the motion sensor is not part of the plurality of individual cells, and the first motion signal of the motion sensor is provided to two or more of the plurality of individual cells.

18. The device of claim 14, wherein the flexible housing is field configurable into a desired shape, and wherein the device further comprises an adhesive for securing the flexible housing in the desired shape adjacent to the desired touchpoint.

19. The device of claim 14, wherein the flexible housing is configured to be flexed in the field into two or more different shapes.

20. A method for disinfecting a desired touchpoint, the method comprising:

receiving a first motion signal indicating motion near the desired touchpoint;

in response to receiving the first motion signal, waiting until motion is no longer detected near the desired touchpoint;

in response to the first motion signal, and in response to motion no longer being detected near the desired touch point, activating one or more UVC LEDs for a predetermined period of time to disinfect the desired touchpoint; and in response to receiving a second motion signal indicating motion near the desired touchpoint while one or more UVC LEDs are activated, turning off any activated ones of the one or more UVC LEDs.

* * * * *